US00PP09156P

United States Patent [19]

Enthoven

[11] Patent Number: Plant 9,156

[45] Date of Patent: Jun. 6, 1995

[54] GERANIUM PLANT NAMED MERIKING

[75] Inventor: Adrianus W. M. Enthoven, Wateringen, Netherlands

[73] Assignee: Enthoven Breeding B.V., Wateringen, Netherlands

[21] Appl. No.: 217,122

[22] Filed: Mar. 24, 1994

[51] Int. Cl.[6] ..... A01H 5/00

[52] U.S. Cl. ..... Plt./87.12

[58] Field of Search ..... Plt. 87.12

[56] References Cited

U.S. PATENT DOCUMENTS

P.P. 5,940 4/1987 Schumann ..... Plt./87.12
P.P. 6,379 11/1988 Craig ..... Plt./87.12
P.P. 7,609 7/1991 Winner ..... Plt./87.12
P.P. 7,641 9/1991 Treis ..... Plt./87.12
P.P. 8,192 3/1993 Holden ..... Plt./87.12
P.P. 8,727 5/1994 Schumann ..... Plt./87.12

*Primary Examiner*—James R. Feyrer
*Attorney, Agent, or Firm*—Foley & Lardner

[57] ABSTRACT

A new and distinct cultivar of geranium named Meriking, particularly characterized by the combined features of red flowers that are semi-double, elliptic flower buds, average flowering time and uniform flowering; inflorescence is open with big flowers; red green to dark at top pedicels; compact plant growth habit; dark green and small foliage and leaf margins that are very slightly incised and double crenated.

3 Drawing Sheets

The present invention comprises a new and distinct cultivar of geranium, botanically known as *Pelargonium zonale,* and hereinafter referred to by the cultivar name Meriking.

Meriking is a product of planned breeding program which had the objective of creating new geranium cultivars with semi-double flower form, compact habit, fast rooting, good tolerance to Botrytis, superior weather resistance, and little need for growth regulators.

Meriking was originated from a hydridization made by the inventor in a controlled breeding program in Wateringen, The Netherlands in 1986. The female parent was a proprietary Enthoven seedling Nr. 15, characterized by its compact growth. The male parent of Meriking was a proprietary Enthoven seedling Nr. 7.12, characterized by its weather resistance.

Meriking was discovered and selected as one flowering plant within the progeny of the stated cross by Adrianus W. M. Enthoven in Jun. 1987 in a controlled environment in Wateringen, The Netherlands.

The first act of asexual reproduction of Meriking was accomplished when vegetative cuttings were taken from the initial selection in Aug. 1987 in a controlled environment in Wateringen, The Netherlands under the supervision of Adrianus W. M. Enthoven.

Horticultural examination of selected units initiated in the spring and summer of 1988, and continuing thereafter, has demonstrated that the combination of characteristics as herein disclosed for Meriking are firmly fixed and are retained through successive generations of asexual reproduction.

Meriking has not been observed under all possible environmental conditions. The phenotype may vary with variations in environment such as temperature, light intensity and day length, without, however, any variation in genotype.

The following measurements and comparison describe plants grown in Wateringen, The Netherlands under greenhouse and outdoor conditions which approximate those generally used in commercial practice.

The following traits have been repeatedly observed and are determined to be basic characteristics of Meriking, which in combination distinguish this geranium as a new and distinct cultivar:

1. The plant has a compact growth habit.
2. The foliage is dark green (RHS upperside 138A–B) and small.
3. The leaf margins are slightly incised and double crenated.
4. The leaf-stalks are relatively short and erect.
5. The flower stems are relatively short and sturdy and extend above the plant.
6. The inflorescence is open with big flowers.
7. The flowers are large in diameter and the flower pedicels are green.
8. The many flower buds are elliptic in shape.
9. The flowers are semi-double and the color is dark red (RHS 43A) with a darker spot (RHS 53D) on the upper face of the upper flower petals and RHS 40A on the lower face with white at point of attachment.
10. The flowering time is average.
11. Plant growth is so controlled that growth regulators are not needed.
12. Due to its compact growth habit, it is possible to grow 20–30% more plants of Meriking per square meter without loss of quality.
13. Plants transport well because of their dark green foliage.

Of the many commercial cultivars known to the present inventor, the most similar in comparison to Meriking is the cultivar Bolero (PEL 107). Reference is made to Chart A which compares certain characteristics of Meriking to those same characteristics of Bolero.

In general comparison to Bolero, Meriking has, among other things, a smaller inflorescence diameter, a much shorter plant height, a much more narrow plant width, and also a much shorter leaf length.

The accompanying color photographic drawings show typical flower and foliage characteristics of Meriking, with colors being as true as possible with illustrations of this type. Scales in centimeters have been added better to show dimensions.

The photo on Sheet 1 is a side view of Meriking grown in a 10.5 cm pot for approximately 8 weeks, showing the foliage, flower stalks and inflorescence.

The photo on Sheet 2 is a close-up view of the upper and lower sides of typical leaves of Meriking.

The photo on Sheet 3 is a close-up view showing the top and bottom of typical flowers of Meriking.

In the following description color references are made to The Royal Horticultural Society Colour Chart (RHS) and Horticultural Colour Chart (HCC). The color values were determined between 2:30 and 2:45 p.m. on Jul. 15, 1988 under 22,300 Klux light intensity at Wateringen, The Netherlands.

Classification:

*Botanical.*—A hybrid of the genus *Pelargonium zonale* cv. Meriking.

*Commercial.*—Zonal geranium.

INFLORESCENCE

A. Umbel:

*Average diameter.*—Indoor: 114 mm.

*Average depth.*—Indoor: 89 mm.

*Peduncle length.*—Indoor: 129 mm.

*Pedicel length.*—Indoor: 34 mm.

*Pedicel color.*—Red-green to dark red at the top.

B. Corolla:

*Average diameter.*—Indoor: 46 mm.

*Form.*—Semi-double (6 to 10 petals and 1–3 petaloids).

*Color (general tonality of a distance of three meters)*-.—RHS 43A, HCC 719.

*Color (main body, upper surface).*—RHS 43A, HCC 719.

*Color (near margin, upper face).*—RHS 43A, HCC 719.

*Color (darker spot upper face upper petals).*—RHS 53D.

*Color (lower side of petal).*—RHS 40A with white at point of attachment.

*Diameter lower petals.*—21 mm.

*Length lower petals.*—25 mm.

*Diameter upper petals.*—18 mm.

*Length upper petals.*—27 mm.

*Petal shape.*—Obovate.

*Sepal color.*—Green with dark-red at the bottom.

C. Bud:

*Shape.*—Elliptic.

*Color.*—Slightly lighter than corolla.

*Pedicel.*—Red-green to dark red at the top.

D. Reproduction organs:

*Androecium.*—7–9 anthers.

*Gynoecium.*—4–5 stigma.

E. Spring flowering:

*Response period.*—In Wateringen, The Netherlands in 1988, 58% of plants had at least 1 open flower 13 weeks after planting unrooted cuttings.

F. Outdoor flower production: The flower count in 1989 in Wateringen, The Netherlands was between 46–51 flowers per plant from June through October observation period.

G. Durability: 100% shatter resistance.

PLANT

A. Foliage:

*Form.*—Kidney shaped, with open base.

*Margin.*—Bicrenate.

*Color.*—Medium green (upperside RHS 138A–B).

*Zonation.*—Absent.

*Length.*—44 mm.

*Diameter.*—81 mm.

*Tolerance of botrytis.*—Good.

B. General appearance and form:

*Internode length.*—35 mm.

*Branching pattern.*—An average of 3.8 branches per plant.

*Height.*—190 mm.

CHART A

COMPARISON OF MERIKING AND BOLERO

| | Meriking | Bolero (PEL 107) |
|---|---|---|
| Plant | | |
| height | very short to short<br>190 mm | short to medium<br>222 mm |
| width | very narrow to narrow<br>302 mm | medium<br>351 mm |
| Leaf blade | | |
| height | very short to short<br>45 mm | medium to long<br>73 mm |
| width | narrow<br>80 mm | medium<br>110 mm |
| Inflorescence | | |
| diameter | small to medium<br>91 mm | large<br>122 mm |
| pedicel length | short to medium<br>33 mm | long to very long<br>45 mm |

I claim:

1. A new and distinct cultivar of geranium plant named Meriking, as illustrated and described.

* * * * *

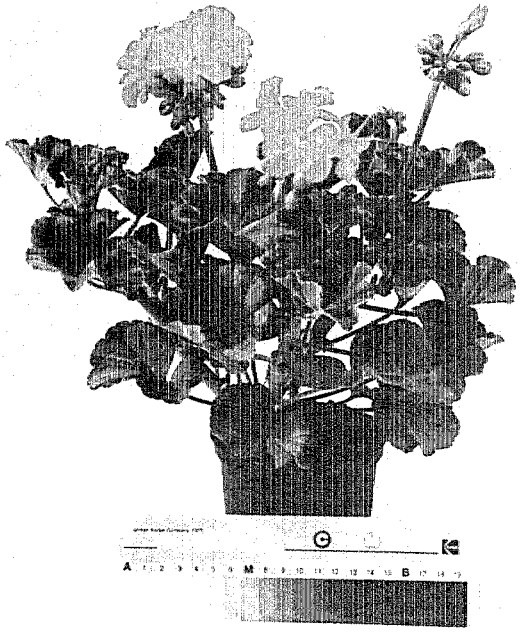

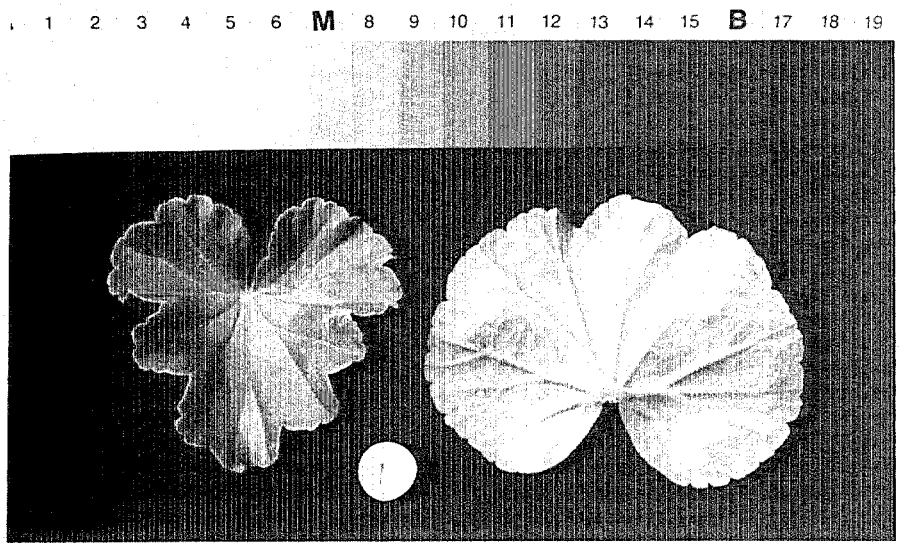
1 2 3 4 5 6 M 8 9 10 11 12 13 14 15 B 17 18 19

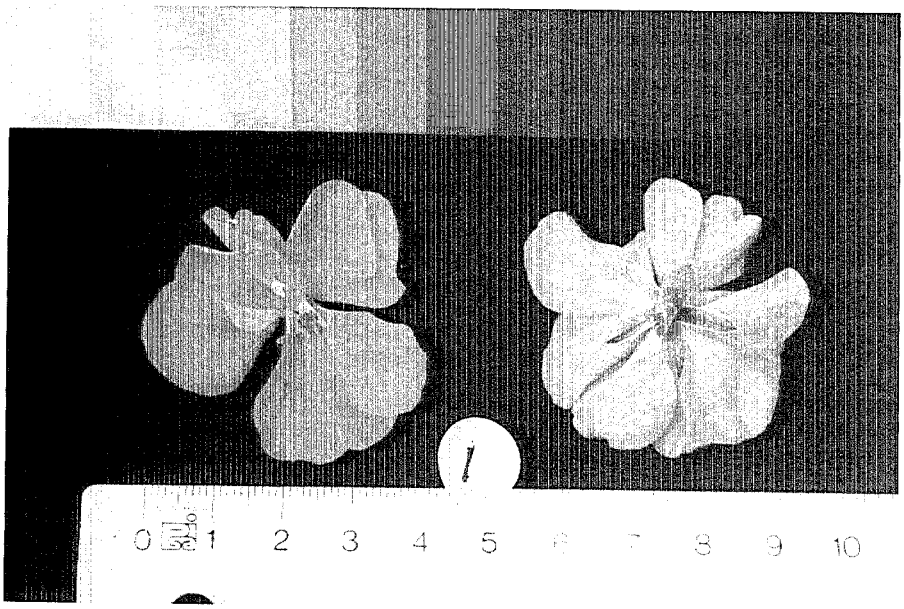
1
0 1 2 3 4 5 8 9 10